United States Patent
Campiche et al.

(10) Patent No.: US 10,561,702 B2
(45) Date of Patent: Feb. 18, 2020

(54) METHOD FOR THE TREATMENT OF SKIN DISORDERS USING DIPEPTIDE DIAMINOBUTYROYL BENZYLAMIDE DIACETATE

(71) Applicant: DSM IP ASSETS B.V., Heerlen (NL)

(72) Inventors: Remo Campiche, Kaiseraugst (CH); Dominik Imfeld, Kaiseraugst (CH); Eileen Jackson, Kaiseraugst (CH); Eliane Ursula Wandeler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/060,096

(22) PCT Filed: Dec. 9, 2016

(86) PCT No.: PCT/EP2016/080469
§ 371 (c)(1),
(2) Date: Jun. 7, 2018

(87) PCT Pub. No.: WO2017/102591
PCT Pub. Date: Jun. 22, 2017

(65) Prior Publication Data
US 2018/0353563 A1 Dec. 13, 2018

(30) Foreign Application Priority Data

Dec. 16, 2015 (EP) .................................... 15200516
Mar. 10, 2016 (EP) .................................... 16159702
May 3, 2016 (EP) .................................... 16168111

(51) Int. Cl.
| | |
|---|---|
| *A61K 38/05* | (2006.01) |
| *A61K 8/64* | (2006.01) |
| *A61Q 19/00* | (2006.01) |
| *A61P 17/10* | (2006.01) |
| *A61P 17/08* | (2006.01) |
| *A61K 8/06* | (2006.01) |
| *A61K 8/55* | (2006.01) |
| *A61K 9/107* | (2006.01) |
| *A61K 47/24* | (2006.01) |

(52) U.S. Cl.
CPC .............. *A61K 38/05* (2013.01); *A61K 8/062* (2013.01); *A61K 8/55* (2013.01); *A61K 8/64* (2013.01); *A61K 9/107* (2013.01); *A61K 47/24* (2013.01); *A61P 17/08* (2018.01); *A61P 17/10* (2018.01); *A61Q 19/008* (2013.01)

(58) Field of Classification Search
CPC ............ A61K 31/4164; A61K 31/4184; A61K 47/02; A61K 47/40; A61K 9/0019; A61K 9/19
See application file for complete search history.

(56) References Cited

U.S. PATENT DOCUMENTS

| | | | |
|---|---|---|---|
| 7,964,630 B2 | 6/2011 | Imfeld et al. | |
| 7,964,639 B2* | 6/2011 | DeLuca | ................. A61K 8/671 514/529 |
| 2009/0111731 A1 | 4/2009 | Imfeld et al. | |
| 2010/0215726 A1* | 8/2010 | Roth | ........................ A61K 8/64 424/450 |
| 2012/0213845 A1 | 8/2012 | Bernstein | |
| 2014/0219942 A1* | 8/2014 | Mendrok-Edinger | ... A61K 8/37 424/70.1 |
| 2014/0309401 A1 | 10/2014 | Hayashida et al. | |
| 2018/0360698 A1* | 12/2018 | Boswell | ............... A61K 8/0208 |
| 2018/0360722 A1* | 12/2018 | Campiche | ................ A61K 8/64 |

FOREIGN PATENT DOCUMENTS

| | | |
|---|---|---|
| CN | 103 505 377 | 6/2015 |
| DE | 20 2012 002309 | 4/2012 |
| WO | 2010/003828 | 1/2010 |
| WO | 2016/154020 | 9/2016 |

OTHER PUBLICATIONS

International Search Report for PCT/EP2016/080469 dated Apr. 10, 2017, 5 pages.
Written Opinion of the ISA for PCT/EP2016/080469 dated Apr. 10, 2017, 10 pages.
Imfeld et al. "557 A peptide derivative with known anti-wrinkle properties was identified as potent dipeptiylpeptidase-4 inhibitor", Journal of Investigative Dermatology, vol. 136, No. 5, May 1, 2016, XP055345491, 2 pages.
"Instant Brightening Moisturiser", MINTEL, Nov. 1, 2011, XP002683631, 4 pages.
"Pentapharm Syn-Ake", Internet Citation, Feb. 26, 2007, XP002472008, 4 pages.
Thielitz et al. "Inhibitors of dipeptidyl peptidase IV and aminopeptidase N target major pathogenetic steps in acne initiation", Journal of Investigative Dermatology, Nature Publishing Group, vol. 127, No. 5, May 1, 2007, XP002476229, pp. 1042-1051.

* cited by examiner

*Primary Examiner* — Marcela M Cordero Garcia
(74) *Attorney, Agent, or Firm* — Nixon & Vanderhye P.C.

(57) ABSTRACT

The present invention relates to a novel use of proline containing dipeptides for the prevention and/or treatment of skin conditions associated with altered, damaged or malfunctioning sebaceous glands.

11 Claims, No Drawings

METHOD FOR THE TREATMENT OF SKIN DISORDERS USING DIPEPTIDE DIAMINOBUTYROYL BENZYLAMIDE DIACETATE

This application is the U.S. national phase of International Application No. PCT/EP2016/080469 filed Dec. 9, 2016, which designated the U.S. and claims priority to EP Patent Application No 15200516.1 filed Dec. 16, 2015, EP Patent Application No. 16159702.6 filed Mar. 10, 2016 and EP Patent Application No. 16168111.9 filed May 3, 2016, the entire contents of each of which are hereby incorporated by reference.

The present invention relates to a novel use of proline containing dipeptides for the prevention and/or treatment of skin conditions associated with altered, damaged or malfunctioning sebaceous glands.

Sebaceous glands are essential components of healthy skin. They produce and secrete sebum, which is responsible for moisturizing and protecting skin and hair. Damaged or malfunctioning sebaceous glands however play a central role in many unwanted dermatological conditions such oily and shiny skin, increased pore size, sebaceous hyperplasia as well as acne vulgaris.

Sebaceous glands can contribute to the development of acne in several ways. One of the most common problems faced by acne sufferers involves overactive sebaceous glands and/or sebaceous hyperplasia (enlarged sebaceous glands). These conditions lead to an overproduction of sebum. The excess sebum however not only leads to oily/shiny skin but also promotes the growth of bacteria that contribute to acne symptoms like *Propionibacterium acnes*. Furthermore, excess sebum can also contribute to keratinized plugs that block the follicle and spur the development of inflammatory lesions.

DPP4 (Dipeptidyl Peptidase IV) inhibitors are described to suppress proliferation of sebocytes (i.e. sebaceous gland cells), to enhance their terminal differentiation and to decrease the total neutral lipid production. Thus, DPP4 inhibitors are said to have the capacity to influence the major pathogenic factors of acne such as sebaceous hyperplasia, follicular hyperkeratosis and inflammation (Thielitz et al. JID (2007), 127; 1042-1051).

Thus, there is an ongoing need for DPP4 inhibitors suitable for skin application which can be used for the prevention or treatment of skin conditions associated with altered, damaged or malfunctioning sebaceous glands.

Surprisingly, it has been found that certain proline containing dipeptides are highly effective DPP4 inhibitors and are able to reduce the sebum production as well as the skin pore size.

Thus, the first object of the present invention relates to a composition comprising at least one DPP4 inhibitor of formula (I)

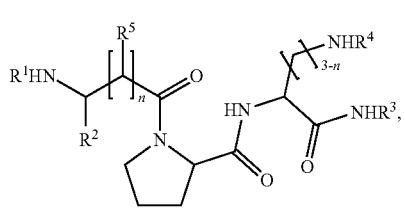

(I)

wherein
n represents 0, 1 or 2,
$R^1$ and $R^4$—independently of each other—are selected from the group consisting of H, $C_1$-$C_6$alkyl, amidino or tetra-$C_1$-$C_6$-alkylamidinium;
$R^2$ is H or $C_1$-$C_6$-alkyl, or $R^1$ and $R^2$ together with the residue to which they are bound form a 5- to 7-membered, saturated ring;
$R^3$ is selected from the group consisting of $C_1$-$C_6$alkyl, ar$C_1$-$C_6$alkyl and heteroaryl$C_1$-$C_6$alkyl; and
$R^5$ is H or, when n is 1, also $NH_2$, or $R^5$ and $R^1$ together with the residue to which they are bound form a 5- to 7-membered, saturated ring;
or a dermatologically acceptable salt thereof for use in the prevention or treatment of disorders of the sebaceous glands such as in particular sebaceous hyperplasia, hyperseborrhea, acne (in particular acne vulgaris), seborrheic dermatitis, atopic dermatitis and rosacea.

In another embodiment, the present invention relates to a cosmetic (nontherapeutic) use of a DPP4 inhibitor of formula (I) for the prevention or treatment of oily and/or shiny skin, blemishes, blotchiness and/or reduction of skin pore size.

As the compounds of formula (I) are highly active DPP4 inhibitors, the present invention also relates to the use of thereof for preventing or treating illnesses or conditions connected with an increased DPP4 activity or capable of being prevented or alleviated by reducing the DPP-IV activity such as e.g. follicular hyperkeratosis, inflammation as well as hyproproliferative disorders (e.g. psoriasis), without being limited thereto.

The term '$C_1$-$C_6$alkyl' as used herein refers to unbranched $C_1$-$C_6$alkyl or branched $C_3$-$C_6$alkyl groups such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl groups.

The term 'ar$C_1$-$C_6$alkyl' as used herein refers to a —$C_1$-$C_6$alkyl-aryl wherein the term 'aryl' is e.g. a phenyl, indanyl or naphthyl group.

The term 'heteroaryl$C_1$-$C_6$alkyl' as used herein refers to a —$C_1$-$C_6$alkyl-heteroaryl wherein the term "heteroaryl" refers to a 5- or 6-membered aromatic ring containing one or more heteroatoms, viz., N, O or S; these heteroaromatic rings may be fused to other aromatic systems.

Examples for the 5- to 7-membered, saturated ring, that $R^1$ and $R^2$ or $R^1$ and $R^5$, respectively, may form together with the residue to which they are bound, are pyrrolidinyl, piperidinyl, piperazinyl, morpholinyl, azepinyl, oxazolidinyl, thiazolidinyl and 1,2,3,4-tetrahydroquinolinyl.

It is well understood, that the present invention encompasses the compounds of formula (I) as optically pure isomers such as e.g. as pure enantiomers or stereoisomers as well as mixtures of different isomers such as e.g. as racemates, or mixtures of diastereoisomers.

The term 'or a dermatologically acceptable salt thereof' refers to compounds of formula (I) in the form of an acid addition salt such as in the form of a chloride, an acetate or a trifluoroacetate salt. Alternatively, the salt may be formed by reaction with an alkali or earth alkaline base resulting in the respective alkali or earth alkaline salt such as in particular the respective lithium, sodium, potassium, magnesium or calcium salts. Most preferred, in all embodiments of the present invention, are the compounds of formula (I) in the form of their acetates or trifluoroacetates. Such salts are easily prepared by a person skilled in the art.

The term 'prevention' as used herein, is not intended as an absolute term. Instead, prevention, e.g., of acne, refers to delay of onset, reduced frequency of symptoms, or reduced severity of symptoms associated with the respective dermatological condition. Prevention therefore refers to a broad range of prophylactic measures that will be understood by those in the art. Similarly, the term 'treatment' is not intended to be an absolute term. In some circumstances, the DPP4 inhibitors according to the invention seek to reduce the sebum production that may e.g. lead to the symptoms of acne. In some circumstances, treatment with the DPP4 inhibitors of the invention leads to a reduction in the frequency or severity of the symptoms.

In all embodiments of the present invention $R^1$, $R^4$ and $R^5$ are preferably H.

In all embodiments of the present invention $R^2$ is preferably H and methyl, most preferably H.

In all embodiments of the present invention $R^3$ is preferably ar$C_1$-$C_6$alkyl, most preferably benzyl.

In all embodiments of the present invention n is preferably 0 or 1, most preferably 1.

Most preferred in all embodiments of the present invention is a compound of formula (I), wherein $R^1$, $R^2$, $R^4$ and $R^5$ are H, $R^3$ is benzyl and n is 1.

The compounds of formula (I) can be prepared as e.g. disclosed in US 2009/0111731.

Particular advantageous in all embodiments of the present invention is the dipeptide having the sequence H-(beta-Ala)-Pro-Dab-NH-benzyl, in particular as diacetate. This compound is also known as Dipeptide Diaminobutyroyl Benzylamide Diacetate (INCI) [CAS 823202-99-9], and is commercially available as SYN®-AKE from DSM Nutritional products Ltd.

In another object, the invention relates to a method for the prevention or treatment of disorders of the sebaceous gland such as in particular sebaceous hyperplasia, hyperseborrhea, acne, seborrheic dermatitis, atopic dermatitis, and rosacea, said method comprises topically administering an effective amount of a pharmaceutical composition comprising at least one DPP4 inhibitor of formula (I) to the appropriate skin area of a person in need of such treatment and optionally appreciating the effect.

In a further object, the invention relates to a method for the prevention or treatment of oily and/or shiny skin, blemishes and/or blotchiness and/or to the reduction of skin pore size, said method comprises topically administering an effective amount of a cosmetic composition comprising at least one DPP4 inhibitor of formula (I) to the appropriate skin area of a person in need of such treatment and optionally appreciating the effect.

The amount of the at least one compound of formula (I) in the respective compositions according to the present invention is preferably selected in the range of 0.5 ppm to 5'000 ppm, preferably in the 2.5 ppm to 250 ppm, most preferably in the range of 25 ppm to 100 ppm, based on the total weight of the composition.

The term 'an effective amount' refers to an amount necessary to obtain the physiological effect. The physiological effect may be achieved by one application dose or by repeated applications. The dosage administered may, of course, vary depending upon known factors, such as the physiological characteristics of the particular composition comprising the at least one compound of formula (I) and its mode and route of administration; the age, health and weight of the recipient; the nature and extent of the symptoms; the kind of concurrent treatment; the frequency of treatment; and the effect desired and can be adjusted by a person skilled in the art. Preferably, the amount of the composition to be applied to the skin is selected in the range of 0.1 to 3 mg/cm$^2$ skin, such as preferably in the range of 0.1 to 2 mg/cm$^2$ skin and most preferably in the range of 0.5 to 2 mg/cm$^2$ skin.

It is well understood that the uses herein, if not stated otherwise, shall in particular refer to a cosmetic, non-therapeutical use intended to beautify the skin, preferably by topical application of a compound according to the present invention to the skin, preferably via a cosmetic composition.

The term 'cosmetic composition' as used herein refers to compositions, which are used to treat, care for or improve the appearance of the skin and/or the scalp. Particular advantageous cosmetic compositions are skin care preparations.

The term 'pharmaceutical composition' as used herein refers to compositions, which are used to treat skin disorders of the sebaceous glands. Particular advantageous pharmaceutical compositions are skin treatment preparations.

The compositions according to the invention are preferably intended for topical application, which is to be understood as the external application to keratinous substances, such as in particular the skin.

As the compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically, respectably pharmaceutically acceptable carrier.

The term 'cosmetically acceptable carrier' respectively 'pharmaceutically acceptable carrier' as used herein refers to a physiologically acceptable medium which is compatible with keratinous substances. Suitable carriers are well known in the art and are selected based on the end-use application. Preferably, the carriers of the present invention are suitable for application to skin (e.g., sunscreens, creams, milks, lotions, masks, serums, hydrodispersions, foundations, creams, creamgels, or gels etc.). Such carriers are well-known to one of ordinary skill in the art, and can include one or more compatible liquid or solid filler diluent, excipient, additive or vehicle which are suitable for application to skin. The exact amount of carrier will depend upon the level of the compound of formula (I) and any other optional ingredients that one of ordinary skill in the art would classify as distinct from the carrier (e.g., other active components). The compositions of the present invention preferably comprise from about 75% to about 99.999%, more preferably from about 85% to about 99.99%, still more preferably from 90% to about 99%, and most preferably, from about 93% to about 98%, by weight of the composition, of a carrier.

The compositions of the present invention can be formulated into a wide variety of product types, including creams, waxes, pastes, lotions, milks, mousses, gels, oils, tonics, and sprays. Preferably the compounds of formula (I) are formulated into lotions, creams, gels, and tonics. These product forms may be used for a number of applications, including, but not limited to, hand and body lotions, facial moisturizers, anti-ageing preparations, makeups including foundations, and the like. Any additional components required to formulate such products vary with product type and can be routinely chosen by one skilled in the art.

If compositions of the present invention are formulated as an aerosol and applied to the skin as a spray-on product, a propellant is added to the composition.

The compositions according to the present invention can be prepared by conventional methods in the art such as e.g. by admixing a compound of formula (I) with all the definitions and preferences given herein with the cosmetically acceptable carrier.

The compositions of the invention (including the carrier) may comprise further conventional adjuvants and additives, such as preservatives/antioxidants, fatty substances/oils, water, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may also comprise further cosmetically active ingredients conventionally used in cosmetic and/or pharmaceutical compositions. Exemplary active ingredients encompass skin lightening agents; UV-filters, agents for the treatment of hyperpigmentation; agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The compositions according to the present invention may be in the form of a suspension or dispersion in solvents or fatty substances, or alternatively in the form of an emulsion or micro emulsion (in particular of oil-in-water (O/W) or water-in-oil (W/O) type, silicone-in-water (Si/W) or water-in-silicone (W/Si) type, PIT-emulsion, multiple emulsion (e.g. oil-in-water-in oil (O/W/O) or water-in-oil-in-water (W/O/W) type), pickering emulsion, hydrogel, alcoholic gel, lipogel, one- or multiphase solution or vesicular dispersion or other usual forms, which can also be applied by pens, as masks or as sprays.

If the composition is an emulsion, such as in particular an O/W, W/O, Si/W, W/Si, O/W/O, W/O/W multiple or a pickering emulsion, then the amount of the oily phase present in such cosmetic emulsions is preferably at least 10 wt.-%, such as in the range of 10 to 60 wt.-%, preferably in the range of 15 to 50 wt.-%, most preferably in the range of 15 to 40 wt.-%, based on the total weight of the composition.

In one embodiment, the compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art.

If the composition according to the invention is an O/W emulsion, then it contains advantageously at least one O/W- or Si/W-emulsifier selected from the list of, glyceryl stearate citrate, glyceryl stearate SE (self-emulsifying), stearic acid, salts of stearic acid, polyglyceryl-3-methylglycosedistearate. Further suitable emulsifiers are phosphate esters and the salts thereof such as cetyl phosphate (e.g. as Amphisol® A from DSM Nutritional Products Ltd.), diethanolamine cetyl phosphate (e.g. as Amphisol® DEA from DSM Nutritional Products Ltd.), potassium cetyl phosphate (e.g. as Amphisol® K from DSM Nutritional Products Ltd.), sodium cetearylsulfate, sodium glyceryl oleate phosphate, hydrogenated vegetable glycerides phosphate and mixtures thereof. Further suitable emulsifiers are sorbitan oleate, sorbitan sesquioleate, sorbitan isostearate, sorbitan trioleate, cetearyl glucoside, lauryl glucoside, decyl glucoside, sodium stearoyl glutamate, sucrose polystearate and hydrated polyisobutene. Furthermore, one or more synthetic polymers may be used as an emulsifier. For example, PVP eicosene copolymer, acrylates/C10-30 alkyl acrylate crosspolymer, and mixtures thereof.

The at least one O/W, respectively Si/W emulsifier is preferably used in an amount of 0.5 to 10 wt. %, in particular in the range of 0.5 to 6 wt.-%, such as more in particular in the range of 0.5 to 5 wt.-%, such as most in particular in the range of 1 to 4 wt.-%, based on the total weight of the composition.

Particular suitable O/W emulsifiers to be used in the compositions according to the invention encompass phosphate ester emulsifiers such as advantageously 8-10 alkyl ethyl phosphate, C9-15 alkyl phosphate, ceteareth-2 phosphate, ceteareth-5 phosphate, ceteth-8 phosphate, ceteth-10 phosphate, cetyl phosphate, C6-10 pareth-4 phosphate, C12-15 pareth-2 phosphate, C12-15 pareth-3 phosphate, DEA-ceteareth-2 phosphate, DEA-cetyl phosphate, DEA-oleth-3 phosphate, potassium cetyl phosphate, deceth-4 phosphate, deceth-6 phosphate and trilaureth-4 phosphate.

A particular suitable O/W emulsifier to be used in the compositions according to the invention is potassium cetyl phosphate e.g. commercially available as Amphisol® K at DSM Nutritional Products Ltd Kaiseraugst.

Another particular suitable class of O/W emulsifiers are non-ionic self-emulsifying systems derived from olive oil e.g. known as (INCI Name) cetearyl olivate and sorbitan olivate (chemical composition: sorbitan ester and cetearyl ester of olive oil fatty acids) sold under the tradename OLIVEM 1000.

In one particular embodiment, the invention relates to compositions with all the definitions and preferences given herein in the form of O/W emulsions comprising an oily phase dispersed in an aqueous phase in the presence of an O/W emulsifier wherein the O/W emulsifier is potassium cetyl phosphate. The amount of oily phase in such O/W emulsions is preferably at least 10 wt.-%, more preferably in the range of 10 to 60 wt.-%, most preferably in the range of 15 to 50 wt.-%, such as in the range of 15 to 40 wt.-%.

The compositions according to the invention in general have a pH in the range of 3 to 10, preferably a pH in the range of 4 to 8 and most preferably a pH in the range of 4 to 7.5. The pH can easily be adjusted as desired with suitable acids, such as e.g. citric acid, or bases, such as sodium hydroxide (e.g. as aqueous solution), triethanolamine (TEA Care), Tromethamine (Trizma Base) and Aminomethyl Propanol (AMP-Ultra PC 2000), according to standard methods in the art.

The following examples are provided to further illustrate the compositions and effects of the present invention. These examples are illustrative only and are not intended to limit the scope of the invention in any way.

EXPERIMENTAL PART

1. Dipeptiyl Peptidase 4 (DPP4) Protease Assay Method

The potential of H-(beta-Ala)-Pro-Dab-NH-benzyl [CAS 823202-99-9], respectively N-Pal-Gly-His-Lys [147732-56-7]/N-Pal-Gly-Gln-Pro-Arg [221227-05-0] (2:1) to inhibit DPP4 was tested using the DPP4 Drug Discovery Kit from Enzo Life Sciences. In brief: DPP4 is pre-incubated for 10 minutes with inhibitors and then added to a quenched fluorogenic substrate (H-Gly-Pro-AMC). Cleavage of the AMC-moiety from the c-terminus of the peptide substrate by DPP4 increases its fluorescence intensity at 460 nm. The AMC signal is then recorded using a fluorescence microplate reader at Ex/Em=380/460 every minute for a total time of 20 min. A "best fit" line is generated with the data points of the first 10-20 min and the slope calculated. The remaining activity in the presence of inhibitor was calculated as follows: % activity remaining (with inhibitor) =(slope of inhibitor-sample/slope of control-sample)*100.

TABLE 1

Results of the protease assay with H-(beta-Ala)-Pro-Dab-NH-benzyl

| c (H-(beta-Ala)-Pro-Dab-NH-benzyl) | | DPP4 activity |
|---|---|---|
| [ppm] | [µM] | [%] |
| 0 | 0 | 100 |
| 0.77 | 1.56 | 74 |
| 1.55 | 3.13 | 58 |
| 3.10 | 6.25 | 40 |
| 6.19 | 12.50 | 24 |
| 12.39 | 25.00 | 14 |
| 24.78 | 50.00 | 7 |
| 49.55 | 100.00 | 4 |
| 99.10 | 200.00 | 2 |

TABLE 2

Results of the protease assay with N-Pal-Gly-His-Lys/N-Pal-Gly-Gln-Pro-Arg (2:1) mixture

| c (N-Pal-Gly-His-Lys/N-Pal-Gly-Gln-Pro-Arg; 2:1)* | | DPP4 activity |
|---|---|---|
| [ppm] | [µM] | [%] |
| 0 | 0 | 100 |
| 0.78 | 1.07 | 119 |
| 1.56 | 2.15 | 118 |
| 3.13 | 4.30 | 106 |
| 6.25m | 8.59 | 92 |
| 12.50 | 17.19 | 116 |

TABLE 2-continued

Results of the protease assay with N-Pal-Gly-His-Lys/N-Pal-Gly-Gln-Pro-Arg (2:1) mixture

| c (N-Pal-Gly-His-Lys/N-Pal-Gly-Gln-Pro-Arg; 2:1)* | | DPP4 activity |
|---|---|---|
| [ppm] | [µM] | [%] |
| 25.00 | 34.37 | 123 |
| 50.00 | 68.74 | 116 |
| 100.00 | 137.48 | 112 |

*Reference (commercially available as MATRIXYL™ 3000)

As can be retrieved from table 1 and 2, only the dipeptide according to the present invention was capable to inhibit DPP4, whereas the reference even stimulated the DPP4 activity.

2. Ex Vivo Assay with Sebaceous Glands (SG)

Organ culture of human sebaceous glands has been performed in order to verify the modulatory activity of H-(beta-Ala)-Pro-Dab-NH-benzyl on sebum secretion. A viability test has been performed in parallel. Human sebaceous glands from skin sample od labia minora have been used (donor: female 37y). The epidermis of the full thickness sample has been carefully removed and the sebaceous glands have been micro-dissected.

The sebaceous glands have been pooled in groups of eight and cultured up to day 6. SGs are cultured in 24 well plate immersed in 500 µl of SGs medium (modified Williams'E medium). After 24 hours the culture medium has been changed and substituted with the medium containing the substance to be tested. The medium has been renewed at day 3 and 5 of culture. At day 6 the glands have been collected and used for the quantification of lipids and proteins. Briefly the SGs have been homogenized in isopropyl alcohol (IPOH) in order to extract lipids and let the protein undissolved. An aliquot of IPOH has been withdrawn to measure the lipids whereas the rest has been evaporated in a vacuum centrifuge. The remaining dry pellet has been minced again in presence of protein lysis buffer. The lipids dissolved in IPOH and the protein dissolved in the lysis buffer have been quantified by infrared spectroscopy (Millipore Direct Detect). The total lipid amount has been obtained by normalizing the quantified lipids upon the quantified proteins (i.e. mg of lipids/mg of proteins).

TABLE 3

Total fat quantification (mg lipid/mg protein)

| SG test sample | untreated | Capsaicin 5 µM | H-(beta-Ala)-Pro-Dab-NH-benzyl 10 µM |
|---|---|---|---|
| 1 | 18.4 | 15.5 | 14.7 |
| 2 | 18.6 | 15.4 | 14.8 |
| 3 | 17.7 | 15.3 | 16.3 |
| 4 | 19 | 15.1 | 15.0 |
| 5 | 16.6 | 15.8 | 13.2 |
| 6 | 16.8 | 15.7 | 13.3 |
| 7 | 16 | 15.7 | 14.6 |
| 8 | 17.1 | 15.5 | 13.5 |
| 9 | 17.3 | 15.7 | 12.9 |
| 10 | 17.5 | 15.6 | 13.0 |
| 11 | 16.6 | 15.6 | 14.4 |
| 12 | 17.8 | 15.4 | 13.2 |
| Average (1-12) | 17.5 | 15.5 | 14.2 |
| S.D. | 1.0 | 0.2 | 1.1 |
| P-value vs untreated t-test | | <0.01 | <0.01 |

Conclusion: H-(beta-Ala)-Pro-Dab-NH-benzyl (10 µM) reduced the sebum secretion ex vivo in sebaceous glands by 19% vs untreated.

3. Clinical Study

A double blind parallel group study was performed with Caucasian female volunteers aged 40-55. 30 volunteers (mean age 46+/−1 year) received a placebo formulation and 29 volunteers (mean age 48+/−1 year) received a *verum* formulation containing SYN®-AKE. The placebo respectively *verum* formulation was applied twice daily for 28 days to face. At the end of the study pictures were taken for computational analysis of pores: 1 photograph of the entire face (90°) was taken with Newtone® Color face for the pore size analysis. Furthermore a questionnaire was filled out by the volunteers.

TABLE 3

| Phase | Ingredients | INCI Name | A Placebo | B Verum |
|---|---|---|---|---|
| A | AMPHISOL ® K | Potassium cetyl phosphate | 1.00 | 1.00 |
|   | Ecorol 16/98P | Cetyl alcohol | 3.00 | 3.00 |
|   | Cutina CP | Cetyl palmitate | 1.50 | 1.50 |
|   | Eutanol G | Octyldodecanol | 3.00 | 3.00 |
| B | Pemulen TR-1 | Acrylates/C10-30 alkyl acrylate cross-polymer | 0.10 | 0.10 |
| C | 1,3-Butylenglycol | Butylene glycol | 3.00 | 3.00 |
|   | Water dem. | Aqua | Ad 100 | Ad 100 |
| D | Dow Corning 345 Fluid | Cyclopentasiloxane, cyclohexasiloxane | 2.50 | 2.50 |
| E | Natriumhydroxid 30% soln. | Aqua, sodium hydroxide | 0.09 | 0.09 |
| F | SYN ®-AKE | Dipeptide Diaminobutyroyl Benzylamide Diacetate, Glycerin, Aqua | 0 | 4.00 |
| G | Euxyl PE 9010 | Phenoxyethanol, ethylhexylglycerine | 1.00 | 1.00 |
| G | Frag 49424902 Chloe | Perfume | 0.05 | 0.05 |

TABLE 4

Results of the computational analysis of the pores

| Number of Pores D0 to D28 | |
|---|---|
| Placebo | +3.2% |
| Verum | −0.8% |
| Conspicuous surface of each pore D0 to D28 | |
| Placebo | −3.2% |
| Verum | −4.4% |
| Conspicuous surface of all pores D0 to D28 | |
| Placebo | +1.5% |
| Verum | −2.7% |
| Conspicuous volume D0 to D28 | |
| Placebo | +3.8% |
| Verum | −1.3% |

As can be retrieved from table 4, the pore size was effectively reduced by the treatment with the *verum* formulation containing a DPP4 inhibitor according to the present invention.

TABLE 5

Results from the computational analysis of gloss

| Contrast Gloss | |
|---|---|
| Placebo | −10.24% |
| Verum | −11.55% |

TABLE 5-continued

Results from the computational analysis of gloss

| Specular Gloss | |
|---|---|
| Placebo | −2.37% |
| Verum | −2.53% |

As can be retrieved from table 5 the gloss (reflecting the oily-/shininess of the skin) was effectively reduced by the *verum* formulation.

TABLE 6

Results from the questionnaire

| | Agree |
|---|---|
| Pore Size Reduction | |
| Placebo | 60% |
| Verum | 69% |
| Non Shiny Skin | |
| Placebo | 60% |
| Verum | 83% |

As can be retrieved from table 6, a perceivable pore size reduction as well as an effective reduction of oily/shiny skin was observed by the volunteers.

The invention claimed is:

1. A method for the treatment of sebaceous gland disorders selected from the group consisting of sebaceous hyperplasia, hyperseborrhea, acne, seborrheic dermatitis, atopic dermatitis and rosacea, wherein the method comprises topically administering to skin area of a person in need of such treatment an effective amount of a pharmaceutical composition comprising a dipeptidyl peptidase IV (DPP4) inhibitory effective amount of dipeptide diaminobutyroyl benzylamide diacetate.

2. The method according to claim 1, wherein the amount of the dipeptide diaminobutyroyl benzylamide diacetate in the composition is in a range of 0.5 ppm to 5,000 ppm, based on the total weight of the composition.

3. The method according to claim 1, which comprises topically applying the composition to the skin area in an amount of 0.1 to 3 mg/cm$^2$ skin.

4. The method according to claim 1, wherein the composition is an O/W emulsion comprising an oily phase dispersed in an aqueous phase in the presence of an O/W emulsifier.

5. The method according to claim 4, wherein the O/W emulsifier is potassium cetyl phosphate.

6. A method for the treatment of oily, shiny, blemished and/or blotchy skin and/or to reduce skin pore size, wherein the method comprises topically administering to skin area of a person in need of such treatment an effective amount of a cosmetic composition comprising a dipeptidyl peptidase IV (DPP4) inhibitory effective amount of dipeptide diaminobutyroyl benzylamide diacetate.

7. The method according to claim 6, wherein the cosmetic composition is a skin care preparation.

8. The method according to claim 6, wherein the amount of the dipeptide diaminobutyroyl benzylamide diacetate in the composition is in a range of 0.5 ppm to 5,000 ppm, based on the total weight of the composition.

9. The method according to claim 6, which comprises topically applying the composition to the skin area in an amount of 0.1 to 3 mg/cm$^2$ skin.

10. The method according to claim 6, wherein the composition is an O/W emulsion comprising an oily phase dispersed in an aqueous phase in the presence of an O/W emulsifier.

11. The method according to claim 10, wherein the O/W emulsifier is potassium cetyl phosphate.

* * * * *